US010656145B2

(12) United States Patent
Post (10) Patent No.: US 10,656,145 B2
(45) Date of Patent: May 19, 2020

(54) DETECTION OF ALLERGENS USING SURFACE-ENHANCED RAMAN SCATTERING

(71) Applicant: General Mills, Inc., Minneapolis, MN (US)

(72) Inventor: Brett Post, Golden Valley, MN (US)

(73) Assignee: General Mills, Inc., Minneapolis, MN (US)

( * ) Notice: Subject to any disclaimer, the term of this patent is extended or adjusted under 35 U.S.C. 154(b) by 531 days.

(21) Appl. No.: 15/374,724

(22) Filed: Dec. 9, 2016

(65) Prior Publication Data

US 2018/0164297 A1    Jun. 14, 2018

(51) Int. Cl.
*G01N 33/53* (2006.01)
*G01N 21/65* (2006.01)
*G01N 33/543* (2006.01)

(52) U.S. Cl.
CPC ....... *G01N 33/5308* (2013.01); *G01N 21/658* (2013.01); *G01N 33/54326* (2013.01)

(58) Field of Classification Search
None
See application file for complete search history.

(56) References Cited

U.S. PATENT DOCUMENTS

| | | | |
|---|---|---|---|
| 7,879,625 | B1 | 2/2011 | Boss |
| 8,361,460 | B2 | 1/2013 | Morimatsu et al. |
| 2001/0007690 | A1 | 7/2001 | Girsh |
| 2006/0286379 | A1* | 12/2006 | Gao ........................ C09C 1/24 428/403 |
| 2009/0258373 | A1* | 10/2009 | Weidemaier ......... C12Q 1/6816 435/7.1 |
| 2010/0055721 | A1 | 3/2010 | Lambert et al. |
| 2010/0210033 | A1* | 8/2010 | Scott .................... G01N 33/543 436/501 |
| 2011/0053283 | A1 | 3/2011 | Hood et al. |
| 2013/0040016 | A1 | 2/2013 | Becker |
| 2013/0115717 | A1 | 5/2013 | Guo et al. |
| 2016/0192683 | A1 | 7/2016 | Arnoff |
| 2016/0243217 | A1 | 8/2016 | Nadeau |
| 2016/0251703 | A1 | 9/2016 | Gilboa-Geffen et al. |
| 2016/0266083 | A1* | 9/2016 | Zhang .................... G01N 33/02 |

FOREIGN PATENT DOCUMENTS

WO         2015066027 A2     5/2015

OTHER PUBLICATIONS

McLintock et al., Universal Surface-Enhanced Raman Tags: Indivdual Nanorads for Measurements from the Visible to the Infrared (514-1064_. ACS Nano, vol. 8, No. 8, 2014, pp. 8600-8609. (Year: 2014).*
Kerbach et al., Managing food allergens in the food supply chain-viewed from different stakeholder perspectives, Quality Assurance and Safety of Crops & Foods, 2009, pp. 50-60. (Year: 2009).*
International Patent Application No. PCT/US2017/063437, International Search Report and Written Opinion dated Feb. 9, 2018, 15 pages.
"Biosensors," Biointerfacial Engineering Research Group, University of Wyoming, Retrieved from the Internet <http://www.uwyo.edu/biointerfacial/biosensors.html> on Dec. 9, 2016, 4 pages.
Cho et al., "Membrane filter-assisted surface enhanced Raman spectroscopy for the rapid detection of E-coli O157: H7 in ground beef," Biosensors and Bioelectronics, vol. 64, 2015, pp. 171-176.
"Dynabeads Protein G Immunoprecipitation Kit," ThermoFisher Scientific, Retrieved from the Internet <https://www.thermofisher.com/order/catalog/product/10007D> on Dec. 9, 2016, 3 pages.
"Magnetic SERS Substrates—Enhanced Reproducibility and Lowered Detection Limit," TechLink, Retrieved from the Internet <http://techlinkcenter.org/summaries/magnetic-sers-substrates-%E2%80%93-enhanced-reproducibility-and-lowered-detection-limit1/1> on Apr. 28, 2016, 1 page.
"Nanopartz in vitro Ramanprobes," Nanopartz, Retrieved from the Internet <https://www.nanopartz.com/invitro_ramanprobes.asp> on Dec. 9, 2016, 2 pages.
Tsai et al., "Detection of rabbit IgG by using functional magnetic particles and an enzyme-conjugated antibody with a homemade magnetic microplate," Chemistry Central Journal, vol. 9, No. 8, Fig. 1, Feb. 22, 2015, Retrieved from the Internet <https://www.ncbi.nlm.nih.gov/pmc/articles/PMC4350001/figure/Fig1/>, 1 page.

* cited by examiner

*Primary Examiner* — Gary Counts
(74) *Attorney, Agent, or Firm* — Fredrikson & Byron, P.A.

(57) ABSTRACT

A technique can be used to detect and/or quantify allergens in foods. In some examples, the technique involves adding magnetic particles that carry antibodies and surface-enhanced Raman scattering (SERS) tags complexed with antibodies to the sample. The antibodies associated with both the magnetic particles and the SERS tags can be selected to bind to one or more antigens that correspond to allergens being investigated. After adding magnetic particles to the sample, a magnetic field can be applied to the sample to concentrate antigens in the sample, including any SERS tags bound to the antigens. The concentrated sample can be analyzed with SERS and a concentration of the mammalian allergen determined based on the SERS response.

22 Claims, 3 Drawing Sheets

DETECTION OF ALLERGENS USING SURFACE-ENHANCED RAMAN SCATTERING

TECHNICAL FIELD

This disclosure relates to techniques for detecting allergens, including techniques for detecting food allergens using surface-enhanced Raman scattering.

BACKGROUND

An allergy is a disorder of the immune system and is characterized by the occurrence of allergic reactions to normally harmless environmental substances. Allergies are caused by antigens. In the case of a food allergy, for example, an individual may experience an adverse immune response to a food allergen. Food allergens are typically naturally-occurring proteins in foods or derivatives that cause the abnormal immune responses. Common food allergens are found in shellfish, peanuts, tree nuts, fish, milk, eggs, soy and fresh fruits.

For example, certain individuals may experience digestive or health problems caused by eating gluten. Gluten is a term commonly used to represent an allergenic class of proteins found in wheat, barley, and rye. Wheat is a grain most commonly found in breads, pastas, and cereal. Wheat often appears in foods like soups and salad dressings as well. Barley is commonly found in beer and in foods containing malt. Rye is most often found in rye bread, rye beer, and some cereals. Individuals that have a wheat allergy or gluten autoimmune disorder caused by Celiac disease need to avoid wheat or gluten in their diet to prevent adverse health effects.

For manufacturers of food products that are labeled as lacking certain common food allergens, regular testing may be performed on product samples to validate the accuracy of the allergen-free claims. One type of test that is typically performed to detect allergens is an enzyme-linked immunosorbent assay, also called ELISA. In an ELISA test, an antigen is immobilized to a solid surface and then complexed with an antibody that is linked to an enzyme. Antigen detection is then accomplished by assessing the conjugated enzyme activity via incubation with a substrate to produce a measureable product. While accurate, ELISA is relatively slow test that typically can only be performed on a limited sample size.

SUMMARY

In general, this disclosure is directed to techniques for detecting and/or quantifying one or more allergens that may be present in a sample. In some examples, the technique is performed on a sample of a product suitable for mammalian consumption, such as a food or beverage product intended for human consumption and/or an ingredient used in the production of such a food or beverage. To detect if an allergen is present in the sample, magnetic particles that each carry an antibody may be added to the sample. The antibody can be selected as one that binds to an antigen corresponding to the allergen of interest. In addition, surface-enhanced Raman scattering (SERS) tags complexed with antibodies can be added to the sample. The SERS tags complexed with antibodies may be formed by bonding an antibody and SERS tag to a carrier particle, such as precious metal nanoparticles. The antibody on the particles that have the SERS tag can be selected as one that binds to the antigen corresponding to the allergen of interest and may be the same or different than the antibody on the magnetic particles.

To detect and/or quantify any allergen antigens present in the sample, a magnetic field can be applied to the sample. The magnetic field can attract each magnetic particle bound to an antigen via an antibody, along with a SERS tag also bound to the antigen via a different antibody. The magnetically attracted material can be separated from residual material, including residual particles containing SERS tags that are unbound to any antigens that may otherwise distort the Raman spectroscopy response if not removed. Once suitably separated, the sample of magnetically concentrated antigens can be analyzed with Raman spectroscopy. The spectrum produced from the magnetically concentrated sample may indicate the number of SERS tags present in the sample which, in turn, can indicate the concentration of antigens corresponding to the allergen in the sample.

Although the specific technique can vary, in some examples, the technique is performed to simultaneously detect and/or quantify multiple allergens that may be present in the sample under analysis. To detect multiple allergens simultaneously, multiple groups of magnetic particles can be added to the sample under analysis. Each group of magnetic particles added to the sample can carry a different antibody selected to bind to a different allergen of interest. In addition, multiple groups of particles that each carry an antibody and a SERS tag can be added to the sample under analysis. Each group of such particles can carry a different antibody selected to bind to a different allergen of interest (e.g., the same types of different allergens targeted by the multiple groups of magnetic particles). After magnetically separating the magnetic particles bound to the antigens from residual sample material, the separated material can be analyzed with Raman spectroscopy. The SERS tags associated with each of the different allergens of interest can cause different shifts to the Raman spectrum, allowing for simultaneous detection and/or quantification of each of the antigens that may be present in the sample.

In one example, a method of detecting allergens using surface-enhanced Raman scattering (SERS) is described. The method includes adding multiple groups of antibody-functionalized magnetic particles to a sample of a human-consumable product or ingredient thereof. Each group of the multiple groups of antibody-functionalized magnetic particles includes an antibody selected to bind to an antigen corresponding to an allergen, and different groups of the multiple groups of antibody-functionalized magnetic particles have different antibodies selected to bind to different antigens corresponding to different allergens. The method also involves adding multiple groups of SERS tags complexed with antibodies to the sample. Each group of the multiple groups of SERS tags includes an antibody selected to bind to the antigen corresponding to the allergen, and different groups of the multiple groups of SERS tags have different antibodies selected to bind to the different antigens corresponding to the different allergens. In addition, the SERS tag for each of the multiple groups of SERS tags are selected so different allergens exhibit different Raman spectrum shifts. The example method also involves concentrating the multiple groups of antibody-functionalized magnetic particles in the sample, including any antigens and SERS tags bound thereto, by application of a magnetic field, thereby producing a concentrated sample. The method further involves analyzing the concentrated sample with SERS, thereby producing a Raman spectrum, and determining a concentration of each of the different allergens in the sample based on the Raman spectrum.

In another example, a method of detecting allergens using surface-enhanced Raman scattering (SERS) is described. The method includes adding sample magnetic particles each carrying an antibody configured to bind to an antigen that is a mammalian allergen. The method also includes adding to the sample particles each having a SERS tag and an antibody configured to bind to the antigen. In addition, the method involves concentrating the antigen in the sample by applying a magnetic field to the sample, thereby producing a concentrated sample, and analyzing the concentrated sample with SERS. The method further involves determining a concentration of the mammalian allergen in the sample based on the SERS analysis performed on the concentrated sample.

In an additional example, a method of managing production of a mammalian consumable products is described. The method involves extracting samples from multiple different consumable product batches or multiple sources of an ingredient incorporated into a consumable product, thereby providing multiple samples. The method also includes combining the multiple samples together to form an aggregate sample and adding to the aggregate sample magnetic particles each carrying an antibody configured to bind to an antigen that is a mammalian allergen. The method also includes adding to the aggregate sample particles each having a SERS tag and an antibody configured to bind to the antigen and concentrating the antigen in the aggregate sample by applying a magnetic field to the sample, thereby producing a concentrated sample. The method also involves analyzing the concentrated sample with SERS and determining a concentration of the mammalian allergen in the aggregate sample based on the SERS analysis performed on the concentrated sample.

The details of one or more examples are set forth in the accompanying drawings and the description below. Other features, objects, and advantages will be apparent from the description and drawings, and from the claims.

DETAILED DESCRIPTION

In general, this disclosure relates to the detection and/or quantification of allergens using surface-enhanced Raman spectroscopy (SERS), which may also be referred to as surface-enhanced Raman scattering. An allergen is typically considered a type of antigen that produces an immune response in which the immune system fights off a perceived threat that would otherwise be harmless to the body. For example, an allergen may be an antigen capable of stimulating a type-I hypersensitivity reaction in atopic individuals through Immunoglobulin E (IgE) responses. To detect and/or quantify an allergen in a sample of interest, the sample may be prepared and analyzed as disclosed herein using SERS. In general, SERS is a vibrational spectroscopy technique that allows for highly sensitive structural detection of low concentration analytes through the amplification of electromagnetic fields generated by the excitation of localized surface plasmons.

A wide variety of materials may be analyzed for allergen detection using the techniques of the present disclosure. Example materials that may be analyzed include consumable foods, beverages, nutritional supplements, and/or ingredients used to manufacture such foods, beverages, and/or nutritional supplements. In some examples, a consumable product that is desirably analyzed for the presence of one or more allergens is a consumable product or ingredient thereof that is intended for mammalian consumption, such as by humans and/or animals (e.g., cats, dogs, horses, cows). Specific examples of products that may be analyzed include animal feed, vitamins, cereal, snack bars (e.g., granola bars, protein bars), bakery items (e.g., bread, cookies, brownies, muffins), bakery mixes, dairy items (e.g., milk, yogurt, cottage cheese), non-dairy substitutes (e.g., dairy-free milk, yogurt, cottage cheese), and any other food, beverage, or supplement that may be desirably analyzed for an allergen. In addition to or in lieu of analyzing a finished consumable product for an allergen, one or more ingredients used to manufacture the product may be analyzed for an allergen. If an allergen is detected above an acceptable level, the ingredient may be repurposed or discarded rather than being incorporated into a product that will then not meet allergen requirements. While the specific ingredient(s) analyzed for one or more allergens will vary depending on the composition of the final product, example ingredients may be analyzed for an allergen include four (e.g., wheat flour), oats, and rice.

Figure 1:
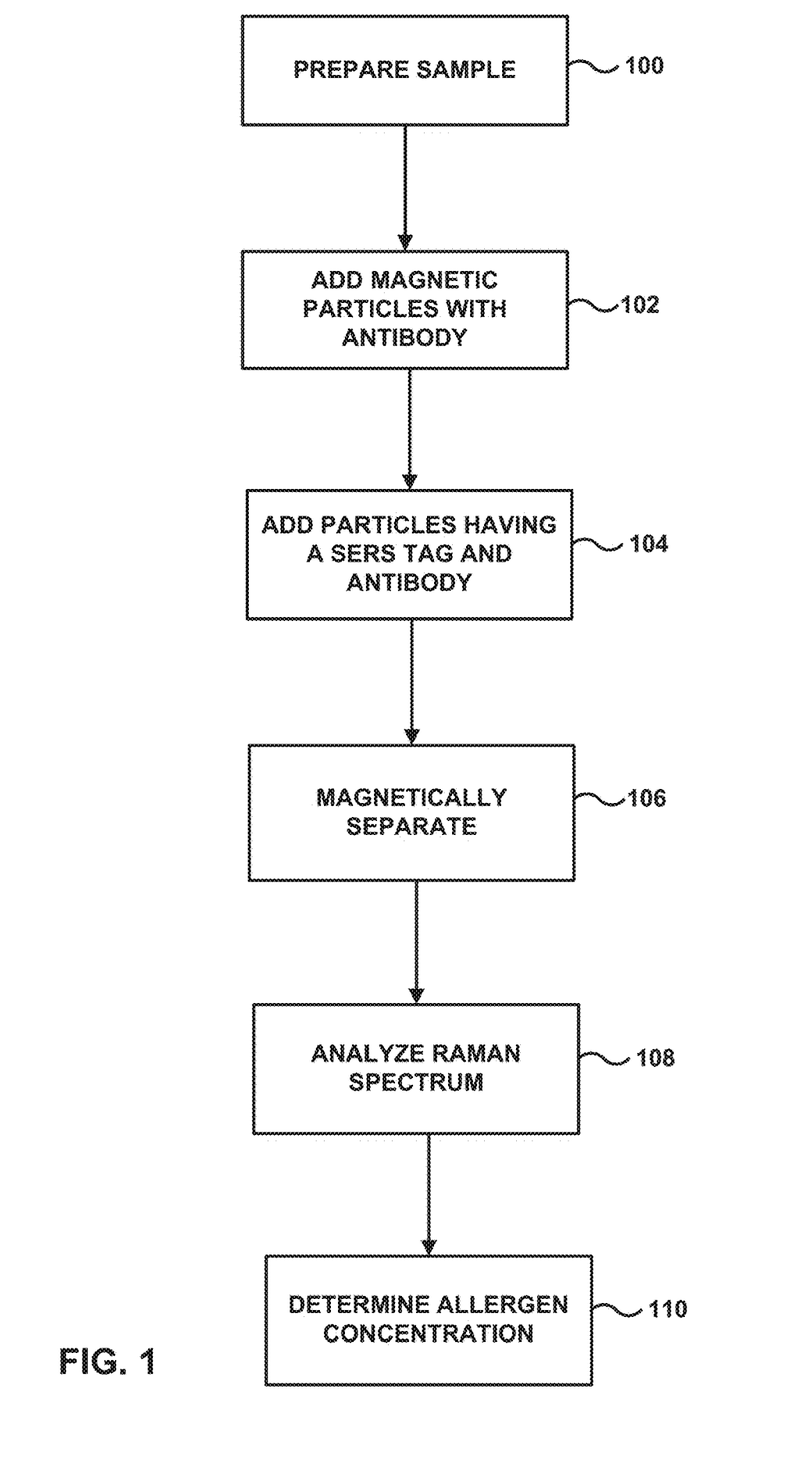
FIG. 1 is a flow diagram illustrating an example technique for detecting one or more allergens in sample.

FIG. 1 is a flow diagram illustrating an example technique for detecting one or more allergens in sample. The process starts by obtaining and optionally processing a sample of interest (100). In some examples, the sample is a human-consumable product or ingredient thereof, including those materials discussed above. In other examples, the sample is not intended for consumption but instead is a material that is inhaled or comes in contact with the surface of the skin in use, such as a lotion, soap, shampoo, perfume, or other material that may contain an allergen that can cause an allergic response to an end user. The sample may be extracted from a single unit of the product or ingredient thereof under investigation (e.g., a single batch or single lot) or may be formed by aggregating samples from different batches or lots, as discussed in greater detail with respect to FIG. 3.

Independent of the source of the sample being analyzed, the sample may or may not be processed in preparation for combination with one or more allergen detection agents. In some examples, the sample is chemically and/or mechanically processed to break the sample down before adding one or more allergen detection agents to the sample. For example, the sample may be ground or milled into a homogeneous powder (e.g., to an average particle size of less than 0.5 millimeters, such as less than 0.2 mm) to increase the surface area of the sample for further processing. Additionally or alternatively, the sample may be processed to extract and purify proteins in the sample to determine if one or more of the proteins in the sample correspond to an allergen. Protein extraction may be performed by precipitating proteins out of the sample and then using a filtration technique, such as centrifugation, to separate extracted proteins from residual matter in the sample. As an example, the sample may be mixed with an aqueous liquid, such as an alcohol and water solution, to extract and/or dilute proteins in the sample for further analysis. As one example, the sample may be mechanically homogenized and then extracted with an ethanol and water solution ranging from 40% ethanol to 70% ethanol.

For instance, in a particular example, the sample may be mechanically homogenized and proteins extracted using 2-mercaptoethanol (e.g., 250 mM) and guanidine hydrochloride (e.g., 2 M) in phosphate-buffered saline (PBS). The extract may be kept at a temperature of approximately 50° C. for 40 minutes and then diluted with 7.5 mL of 80% ethanol, after which the resulting liquid can be vortexed and incubated, for example, for one hour at room temperature in a rotary shaker. Protein extracts can be extracted from residual liquid via centrifugation, providing extract material on which subsequent testing can be performed.

Once suitably prepared, the example technique of FIG. 1 includes combining the sample with antibody-functionalized magnetic particles (102). The antibody-functionalized magnetic particles may be particles that contain a magnetically attractable atom or molecule and one or more antibodies. For example, the antibody-functionalized magnetic particles may include a ferrous metal material such as iron, nickel, cobalt, or other material that can be magnetized and attracted to a magnet. The antibody carried by the antibody-functionalized magnetic particles may be selected based on the type of allergen targeted for detection.

An antibody, also known as an immunoglobulin (Ig), is a large, Y-shaped gamma globulin protein that has a region that binds specifically to a particular antigen. The specific antibody selected can vary depending on the particular antigen (and correspondingly allergen) desired for detection. In the case of human consumable allergens, typical allergens that may be desirably detected include, but are not limited to, a dairy allergen, an egg allergen, a shellfish allergen, a fish allergen, a tree nut allergen, a peanut allergen, a wheat allergen, a barley allergen, a rye allergen, and a soybean allergen. For example, certain consumers may wish to know whether a product being purchased contains gluten, which is a protein typically found in wheat, barley, and rye, among other ingredients.

Each allergen may have one or more specific proteins, or antigens, that trigger an immune response. Example antigens that may be desirably detected to determine the presence of an allergen in a sample under investigation include, but are not limited to, glutenins and/or glaidens (corresponding to a wheat allergen); hordein (corresponding to a barley allergen); secalin (corresponding to rye allergen); vicilins, legumins, and/or albumins (corresponding to a peanut allergen); tropomyosin (corresponding to a shellfish allergen); parvalbumins (corresponding to a fish allergen); beta-lactoglobulin, alpha-lactalbumin, bovine serum albumin, and/or caseins (corresponding to a dairy allergen); and ovomucoid, ovalbumin, and/or ovotransferrin, lysozyme (corresponding to an egg allergen). The antibody associated with each magnetic particle may be selected to bind to a particular antigen associated with a particular allergen of interest.

In some examples, all the particles combined with the sample that have a magnetic component have the same antibodies. In such applications, the allergen detection technique may be executed to detect one specific allergen corresponding to the one type of antibody included with the particles added to the sample. In other applications, however, multiple groups of particles having different antibodies can be added to the sample. Each group of magnetic particles can carry a different antibody corresponding to a different allergen to be detected. For example, where a sample is being analyzed for two allergens, a first group of particles having a magnetic component and a first antibody selected to bind to a first antigen can be added to the sample along with a second group of particles having a magnetic component and a second antibody selected to bind to a second antigen. Thus, the allergen detection technique may be executed to detect a single allergen or multiple different allergens and/or multiple different antigens (e.g., two, three, four, or more allergens). In either application, the number of particles added to the sample may be sufficient to provide an excess number of antibodies relative to the number of antigens expected to be present in the sample.

The antibodies associated with the particles having a magnetic component can be monoclonal antibodies or polyclonal antibodies. Monoclonal antibodies are antibodies from a single antibody producing B cell and therefore only bind with one unique epitope of an antigen. By contrast, polyclonal antibodies are made from multiple different B cells and therefore bind with multiple epitopes on the same antigen. In some examples, the antibodies associated with the particles having the magnetic component that are added to the sample are polyclonal IgG and/or IgE antibodies. Example antibody-functionalized magnetic particles are commercially available from ThermoFisher Scientific under the trade name Dynabeads®.

The technique of FIG. 1 also involves adding a SERS tag complexed with an antibody to the sample under investigation (104). The SERS tag may be directly or indirectly bonded to or otherwise associated with the antibody. A SERS tag may include a plasmonic nanoparticle that generates a strong electric field upon illumination with an appropriate light source and a Raman-active compound (e.g., a Raman active reporter molecule) that confers a distinct spectral signature on the particle. For example, the SERS tag may a precious metal nano particle, such as a gold or silver nano rod or nano sphere. The SERS tag particle may be selected as one that is non-magnetic.

The antibody associated with the SERS tag may be selected based on the type of allergen targeted for detection. For example, the antibody complexed with the SERS tag may be selected to bind to the same antigen or antigens to which the antibodies associated with the magnetized particles are selected to bond. For a particular antigen targeted for detection, the corresponding antibody on the SERS tags may be selected to the bond to the same epitope(s) on the antibody as those antibodies associated with the magnetic particles or may be selected to bond to different epitope(s) on the antibody than those antibodies associated with the magnetic particles.

In some examples, all the SERS tags combined with the sample are complexed with the same antibodies. This arrangement may be useful to detect one specific allergen corresponding to the one type of antibody included with the SERS tags added to the sample. In other applications, however, multiple groups of SERS tags that are each complexed with a different antibody corresponding to a different allergen can be added to the sample. For example, each SERS tag may have an antibody that binds to one specific antigen, and multiple groups of SERS tags each having a different antibody that binds to different specific antigens can be added to the sample. Where a sample is being analyzed for two allergens, for example, a first group of SERS tags complexed with a first antibody selected to bind to a first antigen can be added to the sample along with a second group SERS tags complexed with a second antibody selected to bind to a second antigen. The antigen(s) targeted by the antibody associated with the SERS tag may be the same antigen(s) targeted by the antibody associated with the magnetic particles. In either case, the number of SERS particles with associated antibodies added to the sample may be sufficient to provide an excess number of antibodies relative to the number of antigens expected to be present in the sample.

When multiple groups of SERS tags that each have a different antibody selected to bind to a different specific antigen are added to the sample, the SERS tags in each group may exhibit a different Raman spectral shift from the SERS tags in each other group. However, the SERS tags within each group may be the same and/or exhibit the same Raman spectral shift. This arrangement can be useful to detect multiple allergens simultaneously, for example, allowing different Raman spectral shifts associated with different allergens to be discerned from a single Raman spectrum analysis.

As with the antibodies associated with the particles having a magnetic component, the antibodies associated with the SERS tag can be a monoclonal antibody or a polyclonal antibody. In some applications, the antibodies associated with the SERS tags are polyclonal IgG and/or IgE antibodies, although other antibodies may be used. Example SERS tags complexed with antibodies are commercially available from Nanopartz Inc. in Loveland, Colo. under the trade name Ramanprobes™.

To remove excess SERS tags from the sample that are unbound to an antigen, a magnetic field may be applied to the sample to separate antigen-bound particles from antigen-unbound particles (106). In practice, the antibody-functionalized magnetic particles added to the sample can bind to one or more antigens targeted for detection in the sample. The antibodies associated with the SERS tag can also bind to the one or more antigens targeted for detection in the sample. As a result, antigens in the sample may be bound to both a magnetic particle and a SERS tag through respective antibody binding sites. Excess SERS tags that have not bonded to an antigen will therefore not be bound to a magnetic particle and not be attracted or repelled by a magnetic source, as may be the case with SERS tags bound to an antigen that also carries a magnetic particle. Removing excess SERS tags from the sample can be helpful to detect only those SERS tags bound to antigen molecules being detected.

Any suitable magnetic separation techniques can be used to separate the antibody-functionalized magnetic particles, along with any antibodies and SERS tags bound thereto, from residual sample material. The sample can be exposed to a magnetic field force effective to separate the magnetic particles from nonmagnetic particles, and the residual material (e.g., residual liquid) containing the non-magnetic particles separated (e.g., via centrifugation, decanting, filtration, or other separation technique) from the material containing the magnetic particles. Through the magnetic separation process, the antibody-functionalized magnetic particles in the sample are concentrated, along with any antigens and antibody-complexed SERS tags bound thereto, thereby forming a concentrated sample for further analysis.

In the technique of FIG. 1, the concentrated sample is analyzed with Raman spectroscopy to produce a Raman spectrum (108). Raman spectroscopy is typically performed by directing monochromatic light through the concentrated sample, such a laser light in the visible, near infrared, or near ultraviolet range. The light can interact with molecular vibrations, phonons or other excitations in the sample, resulting in the energy of the light photons being shifted up or down. The shift in energy gives information about the vibrational modes in the system. Electromagnetic radiation from the illuminated sample can be collected with a lens and sent through a monochromator. Elastic scattered radiation at the wavelength corresponding to monochromatic light can be filtered out while allowing the rest of the collected light to be dispersed onto a detector. This can produce a Raman spectrum for the concentrated sample.

The Raman spectrum generated from the concentrated sample can be analyzed to detect one or more allergens in the sample and/or determine a concentration of the one or more allergens (110). Shifts in the Raman spectrum, typically referred to as Raman shifts and reported in wavenumbers, can correspond to vibrational information for specific chemical bonds and molecules. The Raman spectrum can be analyzed using spectral analysis techniques to determine whether a Raman shift corresponding to a specific allergen is present, thus allowing detection of the allergen, and the magnitude of the shift determined, thus allowing the concentration of the allergen to be determined. For example, the Raman shift of the concentrated sample may be compared to the Raman shift of a reference sample having a known concentration of the allergen to determine the concentration of the allergen in the sample under analysis.

In some examples, the Raman shift may correspond to the molecular vibration acquired directly from the target molecule (e.g., antigen), which may be amplified by the addition of the SERS tag. In other examples, the Raman shift may correspond to the molecular vibration acquired from SERS tag bonded to the target molecule rather than the target molecule itself, thereby providing an indirect measurement of the target molecule. In either case, the resulting Raman spectrum can be analyzed (e.g., with reference to calibration information) to detect and/or quantify a concentration of one or more antigens in the sample.

Where the sample is being analyzed to simultaneously detect multiple allergens, each antigen corresponding to each allergen under investigation may exhibit a different Raman shift. For example, the molecular vibration of each antigen and/or the molecular vibration of the SERS tag bonded to each antigen may be different for different antigens. Accordingly, different Raman shifts corresponding to each of the different allergens under investigation may be detected and/or quantified during analysis of the Raman spectrum produced from the concentrated sample. This can allow different allergens in the sample to be simultaneously detected and/or the concentration of such allergens quantified in the sample, e.g., through the generation and analysis of a single Raman spectrum.

Allergen information determined for the sample under investigation can be used in a number of different ways. For example, the concentration of each allergen determined to be present in the sample may be compared to corresponding threshold values to determine if one or more of the allergens exceeds an acceptable limit. If an allergen in the sample is determined to exceed an acceptable limit, a party associated with the manufacturer or distribution of the product from which the sample was taken may modify the production and/or distribution of such product. For example, parties associated with the manufacture of the product from which the sample was taken may discard or repurpose material in the supply chain that provides ingredients used in the manufacture the product, e.g., until it has been determined that the allergen is no longer present in the supply chain. As another example, parties associated with manufacturer of the product may discard or repurpose product believed to potentially contain the allergen above the acceptable limit.

Figure 2:
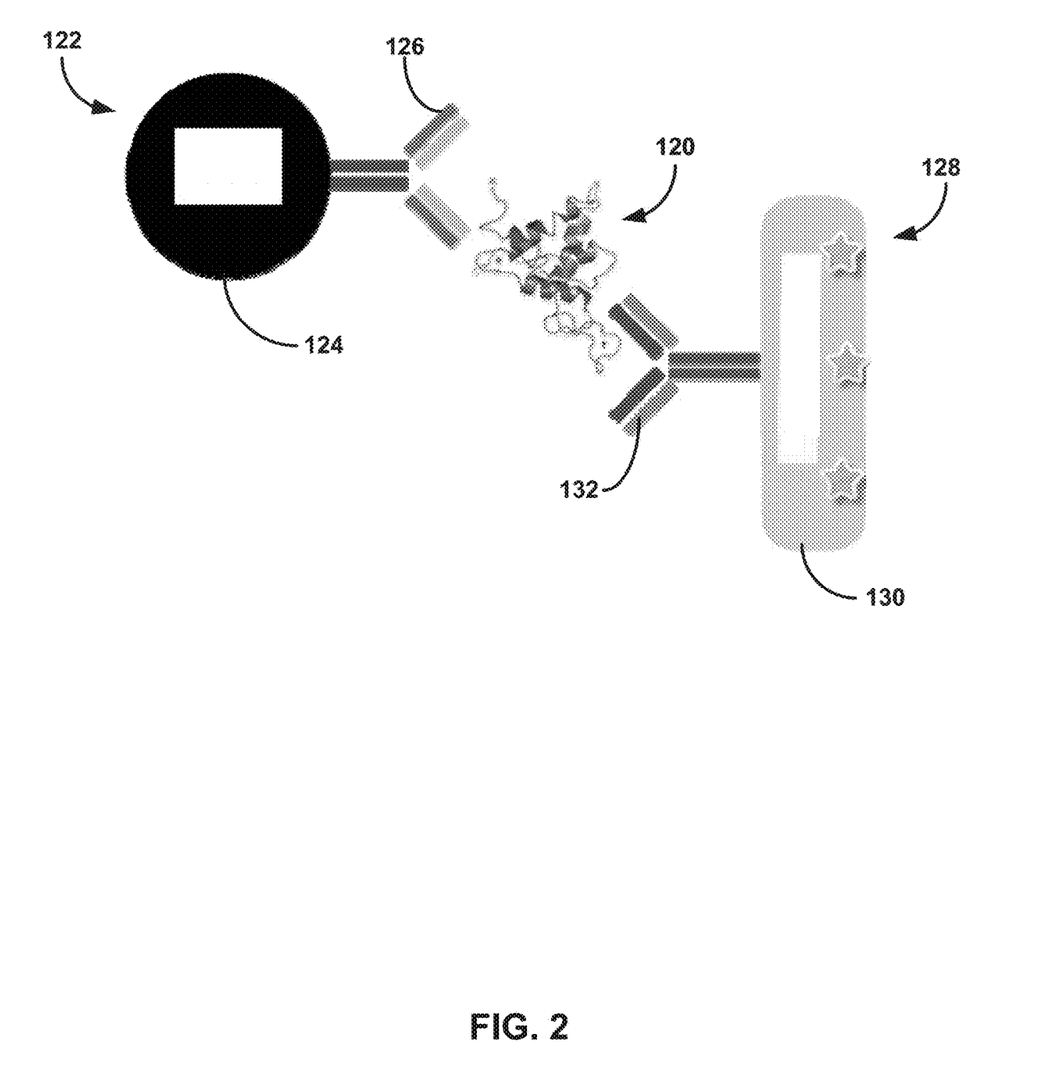
FIG. 2 is conceptual illustration showing how an antigen corresponding to a specific allergen in a sample can be modified to facilitate SERS according to the example technique of FIG. 1.

FIG. 2 is conceptual illustration showing how an antigen corresponding to a specific allergen in a sample can be modified to facilitate SERS. As shown in this illustration, an antigen 120 in the sample may bond with an antibody-functionalized magnetic particle 122. The antibody-functionalized magnetic particle 122 may include a magnetic component 124, such as an iron atom, along with an associated antibody 126. The antibody 126 can bond to the antigen 120, thereby bonding the magnetic component 122 to the antigen. In addition, the conceptual illustration shows a particle 128 that includes a SERS tag 130 complexed with an antibody 132. The antibody 132 can bond to the antigen 120, thereby bonding the SERS tag 130 the antigen. As discussed above, the SERS tag may include a precious metal nano particle and one or more reporter elements that may cause a specific Raman shift during Raman spectroscopy. By exposing the antigen 120 bonded to the magnetic component 124 and SERS tag 130 to a magnetic field, the molecule can be separated from residual, unbound materials, such as excess particles 128 that have not bonded to any antigens 120 in the sample.

As noted above, a variety of different materials may be subject to analysis using the techniques described herein. In some examples, an example technique according to the disclosure is performed on material that is aggregated from multiple sources. In practice, manufacturers of higher volume products that may be subject to allergen certification face practical challenge about how to obtain enough representative samples of a product being manufactured and how to conduct enough tests to determine with appropriate confidence that the product does not contain an allergen above an acceptable level. For example, in the case of higher volume manufacturers of consumable foods, a food product may be manufactured at multiple different physical manufacturing locations. Further, each manufacturing location may receive raw ingredients in high-volume, such as railcars and/or tractor-trailer cars full of raw ingredients. The raw ingredients themselves may come from different source providers. Each point in the supply, manufacturing, and/or distribution chain may provide an opportunity for an allergen source to inadvertently enter the product being manufactured.

While testing of individual ingredient and product samples throughout the supply, manufacturing, and/or distribution chain can help detect if an allergen has inadvertently entered a product, existing allergen detection techniques are limited in the volume of material that can be processed. Commercially available plates for performing enzyme-linked immunosorbent assays (ELISA) typically can only accommodate a small sample size. Further, commercially available ELISA plates can only detect a single allergen at one time, necessitating multiple tests to evaluate the presence of different allergens.

In accordance with examples of the present disclosure, however, an allergen detection technique may be performed on an aggregated sample. The aggregated sample may be obtained from multiple different products and/or different sources of an ingredient used to manufacture the product. The aggregated sample may or may not be of a volume greater than what can be tested using typical commercially available ELISA kits but may allow for the detection of potential allergen contamination across a larger volume of product and/or ingredients.

Figure 3:
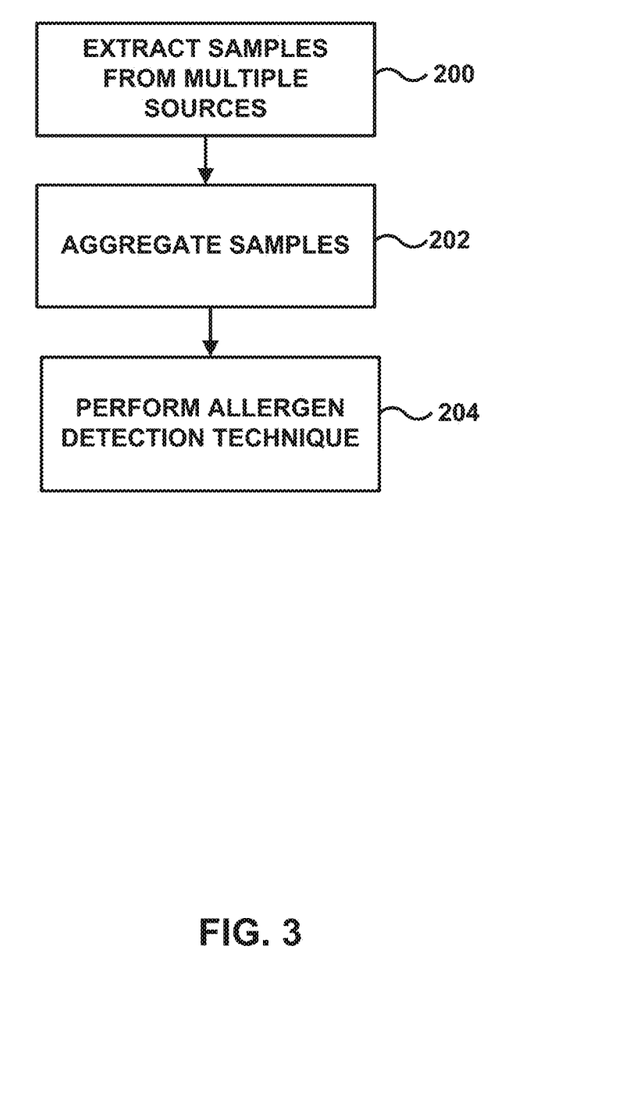
FIG. 3 is a flow diagram showing an example technique for obtaining an aggregate sample and performing an allergen detection technique on that sample.

FIG. 3 is a flow diagram showing an example technique for obtaining an aggregate sample and performing an allergen detection technique on that sample. As shown, the technique involves extracting multiple samples from multiple sources of material to be tested (200). The sources of material to be tested may be different batches of a product being manufactured and/or different sources of an ingredient incorporated into such a product. Each batch may be a defined unit of production, for example, determined based on the location where the product is manufactured, the employee shift manufacturing the product, the manufacturing conditions under which the product is manufactured, or other delineation separating one batch from a different batch. Similarly, each source of an ingredient may be a defined unit of that ingredient, for example, determined based on the location from which the ingredient originated, the transportation container in which the ingredient was transported, the type of ingredient received, or other delineation separating one source of ingredient from a different source.

Any suitable number of samples may be extracted for subsequent testing. In different examples, a sample from at least two different sources may be extracted, such as at least three different sources, at least five different sources, or at least ten different sources. One sample may be taken from each source, or multiple samples may be taken from each of the different sources. In either case, the multiple samples taken from the multiple sources can be aggregated together (202).

The different samples can be aggregated together by physically combining the samples in a single container. Before combining the samples, the samples may or may not be processed, such as mechanically ground. An equal amount of each sample may be added together to form the aggregated sample. Alternatively different amounts of different samples may be combined to form the aggregated sample. For example, the size of each sample may vary in proportion to the size of the source from which the sample was extracted. If a first batch of the product is larger than a second batch of the product, for instance, the aggregated sample may be formed by combining a proportionately larger amount of sample from the second batch than the first batch.

After forming the aggregated sample, an allergen detection technique as described herein can be performed on the aggregated sample or a portion thereof (204). In some examples, the volume of the aggregated sample on which the allergen detection technique is performed is greater than 0.25 grams, such as greater than 0.5 g, greater than 1 g, or greater than 2.5 g. For example, the sample size may range from 0.1 g to 100 g, such as from 0.25 g to 25 g, from 0.5 g to 10 g, or from 1 g to 5 g. The allergen detection technique may be performed to detect and/or quantify a single allergen or multiple allergens simultaneously, as discussed herein. If an allergen in the aggregated sample is determined to exceed an acceptable limit, a party associated with the manufacturer or distribution of the product from which the aggregated sample was taken may modify the production, source ingredients, and/or distribution of such materials as further discussed herein.

Various examples have been described. These and other examples are within the scope of the following claims.

The invention claimed is:

1. A method of detecting allergens using surface-enhanced Raman scattering (SERS) comprising:
adding multiple groups of antibody-functionalized magnetic particles to a sample of a human-consumable product or ingredient thereof, wherein each group of the multiple groups of antibody-functionalized magnetic particles comprises an antibody selected to bind to an antigen corresponding to an allergen, and different groups of the multiple groups of antibody-functionalized magnetic particles have different antibodies selected to bind to different antigens corresponding to different allergens;

adding multiple groups of SERS tags complexed with antibodies to the sample, wherein each group of the multiple groups of SERS tags comprises an antibody selected to bind to the antigen corresponding to the allergen, and different groups of the multiple groups of SERS tags have different antibodies selected to bind to the different antigens corresponding to the different allergens, and wherein the SERS tag for each of the multiple groups of SERS tags are selected so different allergens exhibit different Raman spectrum shifts;

concentrating the multiple groups of antibody-functionalized magnetic particles in the sample, including any antigens and SERS tags bound thereto, by application of a magnetic field, thereby producing a concentrated sample, wherein concentrating the multiple groups of antibody-functionalized magnetic particles in the sample comprises attracting the multiple groups of antibody-functionalized magnetic particles to a magnetic field source and separating residual liquid not attracted to the magnetic field source from the multiple groups of antibody-functionalized magnetic particles attracted to the magnetic field source;

analyzing the concentrated sample with SERS, thereby producing a Raman spectrum; and determining a concentration of each of the different allergens in the sample based on the Raman spectrum.

2. The method of claim 1, wherein the different allergens include at least one allergen selected from the group consisting of a dairy allergen, an egg allergen, a shellfish allergen, a fish allergen, a tree nut allergen, a peanut allergen, a wheat allergen, a barley allergen, a rye allergen, and a soybean allergen.

3. The method of claim 2, wherein the different antigens include at least one protein selected from the group consisting of a glutenins, glaidens, hordein, secalin, vicilins, legumins, albumins, tropomyosin, parvalbumins, beta-lactoglobulin, alpha-lactalbumin, bovine serum albumin, caseins, ovomucoid, ovalbumin, ovotransferrin, lysozyme, and combinations thereof.

4. The method of claim 1, wherein the different antibodies of the multiple groups of antibody-functionalized magnetic particles and the different antibodies of the multiple groups of SERS tags complexed with antibodies each include an antibody selected from the group consisting of polyclonal IgG and IgE antibodies.

5. The method of claim 1, wherein the SERS tags each comprise a precious metal nanoparticle that include a first SERS tag corresponding to a first allergen configured to cause a first Raman spectrum shift a second SERS tag corresponding to a second allergen configured to cause a second Raman spectrum shift different than the first Raman shift.

6. The method of claim 5, wherein the precious metal nanoparticle is a nano rod comprising at least one of gold and silver.

7. The method of claim 1, wherein the sample comprises oats and the different allergens include at least one of rye and barley.

8. The method of claim 1, wherein each particle in the multiple groups of antibody-functionalized magnetic particles comprises a ferrous metal.

9. The method of claim 1, further comprising extracting the sample from a food or beverage supply chain or production line, and modifying operation of the supply chain or production line based on the determined concentration of at least one allergen.

10. A method of detecting allergens using surface-enhanced Raman scattering (SERS) comprising:

adding to a sample magnetic particles each carrying an antibody configured to bind to an antigen that is a mammalian allergen, the mammalian allergen being an allergen that causes an immune response in a mammalian;

adding to the sample particles each having a SERS tag and an antibody configured to bind to the antigen;

concentrating the antigen in the sample by applying a magnetic field to the sample, thereby producing a concentrated sample, wherein concentrating the antigen in the sample by applying a magnetic field comprises attracting magnetic particles bound to the antigen to a magnetic field source and separating residual liquid not attracted to the magnetic field source from the magnetic particles attracted to the magnetic field source;

analyzing the concentrated sample with SERS; and determining a concentration of the mammalian allergen in the sample based on the SERS analysis performed on the concentrated sample.

11. The method of claim 10, wherein adding to the sample magnetic particles each carrying an antibody comprises adding to the sample magnetic particles carrying a plurality of different antibodies configured to bind to a plurality of different antigens that are mammalian allergens;

adding to the sample particles having an antibody comprises adding to the sample particles having a plurality of different antibodies configured to bind to the plurality of different antigens; and determining the concentration of the mammalian allergen in the sample based on the SERS analysis comprises determining the concentration of the plurality of different mammalian allergens.

12. The method of claim 10, wherein the mammalian allergen is an allergen present in at least one of a human-consumable food and beverage.

13. The method of claim 12, wherein the mammalian allergen is at least one of a dairy allergen, an egg allergen, a shellfish allergen, a fish allergen, a tree nut allergen, a peanut allergen, a wheat allergen, a barley allergen, a rye allergen, and a soybean allergen.

14. The method of claim 10, wherein the antigen is a protein selected from the group consisting of a glutenins, glaidens, hordein, secalin, vicilins, legumins, albumins, tropomyosin, parvalbumins, beta-lactoglobulin, alpha-lactalbumin, bovine serum albumin, caseins, ovomucoid, ovalbumin, ovotransferrin, lysozyme, and combinations thereof.

15. The method of claim 10, wherein the sample comprises oats and the mammalian allergen is at least one of rye and barley.

16. The method of claim 10, wherein the magnetic particle comprises iron.

17. The method of claim 10, wherein determining the concentration of the mammalian allergen in the sample comprises comparing a SERS response for the concentrated sample to a SERS response for a reference sample having a known concentration of the mammalian allergen.

18. The method of claim 10, wherein each particle having a SERS tag and an antibody is a precious metal nanoparticle.

19. The method of claim 18, wherein the precious metal nanoparticle is a nano rod comprising at least one of gold and silver.

20. The method of claim 10, wherein the antibody carried by each of the magnetic particles is selected from the group consisting of polyclonal IgG and IgE antibodies, and the antibody associated with each of the sample particles is selected from the group consisting of polyclonal IgG and IgE antibodies.

21. The method of claim 10, further comprising at least one of chemically and mechanically breaking down the sample before adding the magnetic particle carrying the antibody and the SERS tag carrying the antibody to the sample.

22. The method of claim 10, further comprising extracting the sample from at least one of a food supply chain and production line, and modifying operation of the supply chain or production line based on the determined concentration of the mammalian allergen.

* * * * *